United States Patent [19]

Song

[11] 4,358,908
[45] Nov. 16, 1982

[54] PLANT CULTURE VESSEL

[76] Inventor: John S. Song, 2827 Sheridan Pl., Evanston, Ill. 60201

[21] Appl. No.: 219,846

[22] Filed: Dec. 23, 1980

[51] Int. Cl.³ .............................................. A01G 9/02
[52] U.S. Cl. ........................................... 47/66; 47/87;
220/305; 220/366; 220/371; 220/373; 435/284;
435/287; 435/311
[58] Field of Search ................. 47/1.1, 14, 16, 59,
47/60, 61, 69, 85, 87; 220/366, 305, 326,
371–374; 435/284, 287, 296–301, 311, 313, 809,
810

[56] References Cited

U.S. PATENT DOCUMENTS

| | | | |
|---|---|---|---|
| 835,012 | 11/1906 | Craig | 220/366 X |
| 1,367,164 | 2/1921 | Miller | 220/366 |
| 1,513,360 | 10/1924 | Ablahadian | 435/296 X |
| 3,297,184 | 1/1967 | Andelin | 435/296 X |
| 4,012,288 | 3/1977 | Lyman et al. | 435/284 |
| 4,038,149 | 7/1977 | Liner et al. | 435/298 X |
| 4,121,525 | 10/1978 | Courtis | 47/59 X |
| 4,224,765 | 9/1980 | Song | 47/85 |
| 4,231,489 | 11/1980 | Malone | 220/366 X |
| 4,252,268 | 2/1981 | Haire | 220/366 X |

FOREIGN PATENT DOCUMENTS 2362580  3/1978  France .................................. 47/85

Primary Examiner—James R. Feyrer
Attorney, Agent, or Firm—Howard H. Darbo

[57] ABSTRACT

A cap and a base fit together to form the culture vessel. Adjacent the tops of the walls of the base is a rim which is "L" shaped in cross-section, consisting of a bottom leg joined to the base walls and an upright leg. Downwardly extending walls of the cap project into the space between this flange and the walls of the base. These cap walls have a plurality of spaced ribs which frictionally engage the walls of the base so that the cap will maintain a position in which it is slightly raised above the position wherein the cap is fully seated against the base. When in that raised position a length of cotton filtering material may be used between the bottoms of the cap walls and the bottom leg of the rim. The cap has an outside peripheral flange coplanar with the upright leg thereby permitting pressure sensitive tape to be applied to the two and bridging the space therebetween. Extending downwardly from the top, within the base walls and adjacent thereto, is a condensate drip flange.

9 Claims, 6 Drawing Figures

PLANT CULTURE VESSEL

BACKGROUND AND SUMMARY OF THE INVENTION

The present invention relates to a vessel for use in growing plant tissue cultures, e.g., plant tissue, parts of plants or plants.

In the growing of plant tissue cultures, it is likely that the grower will want to provide various growth conditions at various stages of the plant growth. Such conditions may include, for example, a condition under which the container is hermetically sealed, a condition under which the container is allowed to breathe only to a very limited extent, a condition under which air is allowed to pass freely into and out of the closed container but with the air going into the container being filtered to remove possible contamination. Vessels for this purpose are known. An example of such a known vessel is illustrated by my prior U.S. Pat. No. 4,224,765.

A principal object of the present invention is to provide an economical vessel which is readily adaptable by the grower to provide any of the variety of growing conditions as may be desired by the grower. Economy is not only present insofar as the cost of manufacture is concerned (and thus the grower's acquisition cost) but also from the standpoint of efficient use of the area or space that a grower has available to be occupied by plant culture vessels. An additional consideration for the grower is the problem of sterilizing the vessel prior to its use and embodiments of the present invention are well suited to receive that treatment.

Further objects and advantages will become apparent to those knowledgeable in the art from the following description and the drawings hereof.

In the present invention the cap has walls which extend down beside the side walls of the base member and into a space about those side walls which is defined by an "L" shaped rim on the outside of the side walls. The walls of the cap have ribs which frictionally engage the side walls of the base member thereby permitting the cap to be positioned with its cover slightly above the side walls of the base member and in a position such that an air passage is provided into and out of the vessel. When so positioned, a ring of filtering material may encircle the walls of the base member, in the bottom of the space defined by the "L" shaped rim, for the purpose of clarifying the air moving into the vessel.

DESCRIPTION OF SPECIFIC EMBODIMENT

The following disclosure is offered for public dissemination in return for the grant of a patent. Although it is detailed to ensure adequacy and aid understanding, this is not intended to prejudice that purpose of a patent which is to cover each new inventive concept therein no matter how others may later disguise it by variations in form or additions or further improvements.

Figure 1:
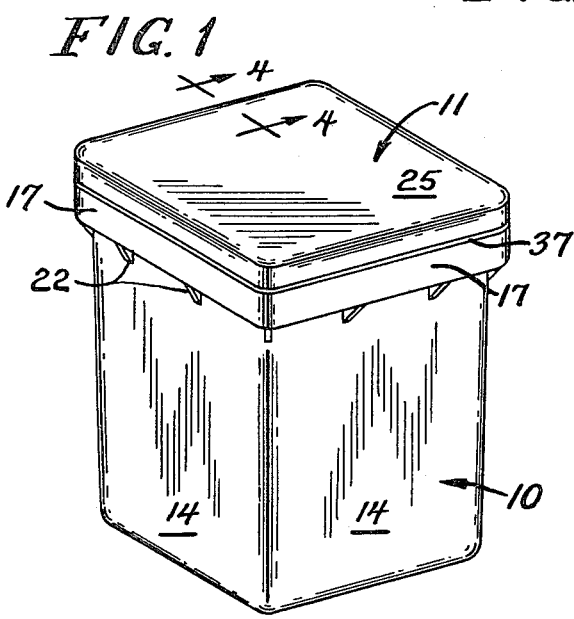
FIG. 1 is an isometric view of an embodiment of the invention.
Figure 2:
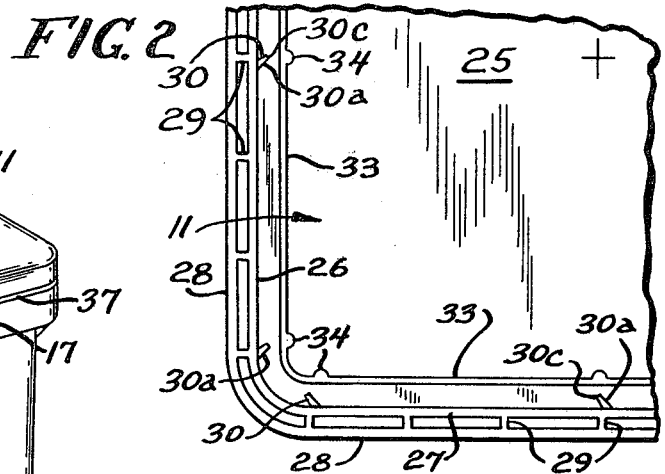
FIG. 2 is a view looking at the underside of a portion of the cap.
Figure 3:
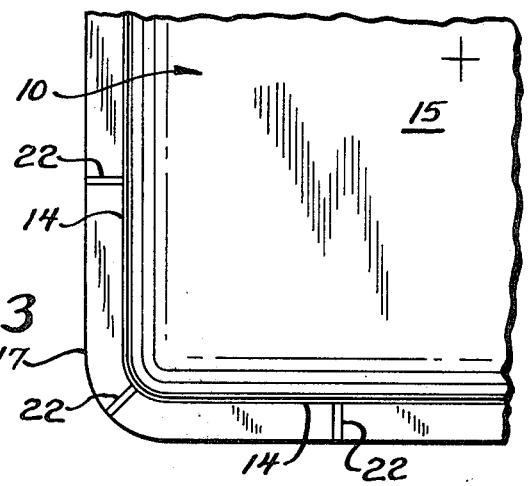
FIG. 3 is a view looking upward from below a portion of the base.

A vessel in accordance with the present invention comprises two components, a base, generally 10, and a cap, generally 11. When the base and cap are mated together as illustrated in FIG. 1, they define an enclosure or chamber 12 which can be used for the culturing of plants. The configuration is substantially square in horizontal cross-section. While they may be made in various sizes, I believe that an appropriate size for the chamber would be to have the square dimension of the chamber equal to about $2\frac{5}{8}$ inches (6.67 cm) and to have its height $3\frac{7}{8}$ inches (9.84 cm). The vessel should be transparent, or at least translucent so that light can enter. The base would be made of a rigid plastic, such as polycarbonate, while the cap or cover would be made of a semi-flexible plastic such as polypropylene. Such a vessel is light in weight and virtually unbreakable.

Figure 4:
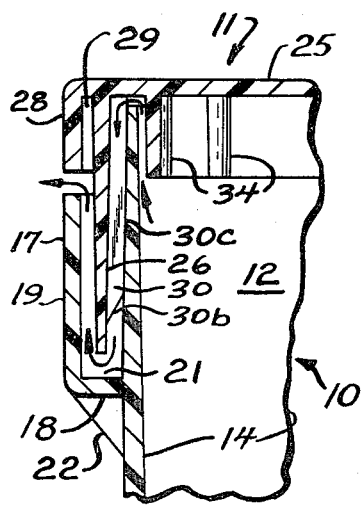
FIG. 4 is a partial section as seen at line 4—4 of FIG. 1.
Figure 5:
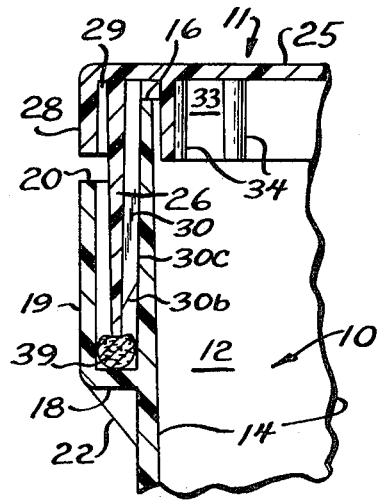
FIG. 5 is a view similar to FIG. 4 but showing the use of a filter.
Figure 6:
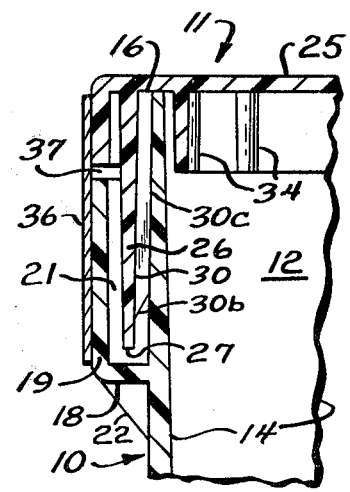
FIG. 6 is a view similar to FIG. 4 but showing the vessel hermetically sealed by a tape.

The base has four upright walls 14 which stand substantially vertically upright from the bottom 15. The walls terminate in tops 16 which lie in a common plane. An annular rim 17 encircles the base a short distance below the tops of the walls. As best seen in FIGS. 4-6, this rim is generally "L" shaped in cross-section and consists of a bottom leg 18 joined to the walls 14 and an upright leg 19. All about the base the upright leg of the rim terminates in a top 20 which is in a plane below the plane of top 16. The rim defines a space 21 between it and the walls 14. Spaced gussets 22 are employed between the bottom leg 18 and the walls 14 for reinforcement.

The cap 11 comprises a planar top 25 with walls 26 extending downwardly therefrom and positioned to be about centrally received in the space 21 defined by the rim. These walls have bottoms 27 lying in a common plane. As best seen in FIG. 6, the plane of these bottoms is above the bottom leg 18 of the rim when the cap is fully seated on the base, as illustrated in FIG. 6. A peripheral wall 28 is just outside of the walls 26 with its outer face substantially coplanar with the outer face of the upright legs 19 of the rim. At spaced intervals there are reinforcing webs 29 between the walls 26 and 28. At spaced intervals about the inside of walls 26 are a plurality of ribs 30 projecting inwardly. These ribs are not at right angles to the walls 26 but one face 30a thereof is approximately at forty-five degrees (included angle) between it and the walls 26. The proximal side of the ribs is thicker than the distal edge. At the bottom the ribs are tapered as seen at 30b to facilitate initially fitting the cap onto the base. The distal edge projects outwardly sufficiently so as to firmly engage the outside of walls 14 of the base when the cap and base are mated. The angular positioning of the ribs, plus the fact that the cap is formed from a plastic having some resiliency, allows the ribs to flex as the cap is mated onto the base and provides a spring action which ensures that the ribs maintain a significant frictional engagement with the walls 14. Spaced inwardly of the ribs is an annular flange 33 on the cap. This flange has a plurality of spaced reinforcing ribs 34.

FIG. 6 illustrates the manner in which the vessel would be used when it was desired that the chamber 12 be hermetically sealed. A length of pressure sensitive tape, as for example made of plastic or cloth impregnated plastic, is affixed to the outer faces of peripheral wall 28 and the upright leg 19 of the rim so as to completely cover the gap 37 therebetween. In some instances the grower will not want full hermetic sealing and in that instance the tape 36 would not be employed, but the cap 11 would be fully seated on the tops of the walls 14 in the manner illustrated in FIG. 6. Even though such complete seating existed, there would be some avenues for the passage of air therebetween due to the fact that the contact faces between the two were not perfect. Thus as the ambient air pressure changed there would be some breathing through those minute avenues. Of course, if the tape 36 is employed such breathing can be virtually eliminated.

If the grower desires additional breathing for the vessel, he would raise the cap slightly above the top 16 of the walls 14 in a position such as that illustrated in FIG. 4. Now, as indicated by the arrows in FIG. 4, air can move rather freely into and out of the container since there is a passageway between the top 16 of the walls and the top 25 of the cap, as well as through the space 21 at both sides of the walls 26 of the cap. Oftentimes the grower will want to sterilize the vessel before it is used to eliminate contamination. When such sterilization is performed by autoclaving the cap would be positioned upwardly as illustrated in FIG. 4 to permit the vessel to breath during the autoclaving.

Oftentimes the grower will desire to permit the vessel to breathe, but will not want air-borne contamination to enter the vessel as air circulates into the vessel. In that event a length of filtering material would be inserted into the space 21 and completely encircling the walls 14. This could be a length having the appearance of a rope or could be in the form of a gasket ring. It could be made of one of the various types of known filtering materials, such as cotton or an open-cell plastic. As illustrated in FIG. 5, the filter is of such a size as to be pressed between the bottoms 27 of walls 26 and the bottom leg 18 of the rim even though the cap is in the slightly raised position so that there is a gap between the top 25 and the top 16 of the walls 14. Thus the air can circulate in the manner illustrated by the arrows in FIG. 4, but in doing so that air must pass through the filter 39. Thereby the presence of the filter will act to remove at least most of the air-borne contaminates from air moving into the container (i.e., air moving in the reverse of the directions indicated by the arrows in FIG. 4).

Generally, moisture in the air in the vessel will at times condense on the underside of the top 25. It would be undesirable to have that condensed moisture move across the underside of the top and descend into the space 21 to be absorbed by the filter 39. The flange 33 will cause such moisture to fall down inside the vessel rather than getting out to the walls 26 where it would descend to the filter.

It will be noted that the length of the air passageway, as illustrated in FIG. 4, is nearly double the vertical dimension of the walls 26, and that two "U" shaped turns are present in that passageway. As a result thereof, even though a filter 39 is not employed in the passageway it is somewhat difficult for air suspended contaminates to get into the vessel. Another feature to be noted is that the tape 36 is relatively easy to apply since the outer faces of the peripheral wall 28 and the upright leg 19 are coplanar. These features can be accomplished merely by adding less than 3/16 of an inch (i.e., less than 0.476 mm) all around the vessel; that is, the extent to which the outer face of leg 19 extends beyond the outer face of the wall 14 of the container. Obviously, this can be a saving of shelf space in a laboratory.

I claim:

1. A container for use in culturing plants and comprising a base member and a cap member which are mated to form an enclosure;
    said base member having upstanding wall means defining a base top;
    said cap member having a top and an outer wall extending downwardly therefrom outside of said wall means, with at least the lower portion of said outer wall being spaced a selected distance from said wall means;
    said cap member further having an annular flange projecting downwardly from said top inside of and in juxtaposition to the wall means to block the flow of condensation on the inside of said cap top outwardly past said wall means; and
    a plurality of downwardly extending and transversely spaced flexible ribs integral with said outer wall and positioned within the space defined between said outer wall and said wall means and extending into functional engagement with said wall means, said ribs projecting from said outer wall in a manner such that the included angle therebetween is substantially less than ninety degrees;
    whereby said outer wall and ribs are adapted to securely retain said cap mated with said base member with the tops of said cap and base member in sealing engagement and so that said ribs will flex to accommodate base members having varying sizes.

2. A container in accordance with claim 1 wherein filter material is positioned between said wall means of said base member and said outer wall of said cap so that air flow into said base member must pass through said filter material.

3. A container for use in culturing plants and comprising a base member and a cap member which are mated to form an enclosure, said base member having upstanding walls having tops in a first common plane, said cap member having a top with walls extending downwardly therefrom which are outside of and in juxtaposition to the upstanding walls, said cap member walls having bottoms in a second common plane, said container being characterized by:
    said base member having a rim thereabout which rim is generally "L" shaped in cross-section and consists of a bottom leg joined to the base member walls and an upright leg which terminates in a third plane which is below said first plane and above said second plane, said rim defining a space between said upright leg and said upstanding walls;
    said top being seated against said tops of said upstanding walls, said downwardly extending walls extending into said space;
    one of said members having a plurality of spaced ribs integral with the walls thereof and projecting toward and into frictional engagement with the walls of the other member, whereby when the cap member is raised so that the top is spaced a short distance above the tops of said upstanding walls the frictional engagement of said ribs will hold the cap member in that raised position and with the cap member so raised air can flow between said top and the tops of said upstanding walls and through said space at each side of said downwardly extending walls to thereby allow the container to breathe.

4. A container as set forth in claim 1, wherein said one member is the cap member.

5. A container as set forth in claim 4, wherein said ribs project from the downwardly extending walls in a manner such that the included angle therebetween is substantially less than ninety degrees, and wherein the ribs have tapered bottoms.

6. A container as set forth in claim 1 and for use with a length of pressure sensitive tape, said container being further characterized by:

the cap member including a peripheral wall substantially coplanar with an outside face of said upright leg, whereby said length of tape may be affixed to said peripheral wall and outside face and bridging any space therebetween to provide a fluid tight seal for said container.

7. A container as set forth in claim 6 in combination with a length of filter material, said material being positioned in said space and resting on said bottom leg and, with said cap member in said raised position, said material abutting said bottoms of said cap member walls whereby said air flow must pass through said filter material.

8. A container as set forth in claim 1 in combination with a length of filter material, said material being positioned in said space and resting on said bottom leg and, with said cap member in said raised position, said material abutting said bottoms of said cap member walls whereby said air flow must pass through said filter material.

9. A container as set forth in claim 8, wherein said cap member includes an annular flange projecting downward from said top, said annular flange being inside of and in juxtaposition to the upstanding walls, whereby condensation on a central part of said top will not flow outwardly to said downwardly extending walls and thus into said space.

* * * * *